Jan. 8, 1963 F. W. ANDERSON Plant Pat. 2,208

ALMOND TREE

Filed March 20, 1961

WITNESS

Addison E. Avery

INVENTOR

Frederic W. Anderson

Webster & Webster

ATTYS.

United States Patent Office

Plant Pat. 2,208
Patented Jan. 8, 1963

2,208
ALMOND TREE

Frederic W. Anderson, Merced, Calif., assignor to Kim Bros., doing business as Reedley Nursery, Reedley, Calif., a copartnership Filed Mar. 20, 1961, Ser. No. 97,118
1 Claim. (Cl. 47—62)

This invention relates to a new and distinct variety of heavy-producing almond tree which blooms later than any of the present commercial varieties, and yet has many of the desirable characteristics thereof.

One of the principal objects of my long and continuing almond breeding program in my experimental almond orchard near Le Grand, County of Merced, California, and wherein several thousand seedlings from crosses are grown annually, has been to obtain such later blooming varieties. The purpose is to lessen the heavy losses due to late rains and frosts, and to reduce the large costs of spraying and heating to alleviate such losses. Also—by later blooming—pollinization is more likely due to the greater activities of bees and other insects which are essential for cross pollination; all present commercial varieties of almonds being self-sterile and requiring cross pollination in order to set nuts.

In comparison with other varieties:

The Ruby (U.S. Plant Patent No. 1698) blooms a day or two later than the Texas (also known as "Mission" and unpatented), and the present variety extends the blooming period three to five days later; the blooming period thus being about with the July Elberta peach (U.S. Plant Patent No. 15) and a little later than the Tilton apricot and Santa Rosa plum (both unpatented). These last three identified varieties are grown rather extensively in the interior valley of California without the necessity of frost protection. Accordingly, it seems probable that the present variety will bear profitable crops likewise without such protection. In fact, experimental trees of the present variety have, since coming into bearing, borne excellent crops without protection of any kind. It also produced a full crop in a year when rains during the blooming period of the commercial varieties reduced the crop of almonds in California by more than 60%.

Compared to the Nonpareil (unpatented), long the leading almond variety in California, the present variety blooms on the average about ten days later; has a comparable tree but with a better spur system; and bears nuts which have averaged slightly smaller, probably because of the heavier crops borne. The kernel shell-out percentage has averaged about 55% as compared with an average of 65% for the Nonpareil and 45% for the Texas. The shell of the present variety is somewhat heavier and much better sealed, and accordingly is more protected from damage by birds, insects, fungi, and moisture. The kernels average about twenty-eight to the ounce; the thickness is approximately 7.6 millimeters, or about the same as the Nonpareil; the shape is slightly longer and narrower; and the kernels are slightly darker in color and often show some striations.

The present variety is interfertile with both the Texas and Ruby, and there is sufficient overlapping in blooming periods to insure adequate cross-pollination of all three.

The present variety of almond tree was originated in my experimental orchard, located as aforesaid, as a seedling resulting from a cross between the Texas, and an unnamed seedling resulting from a cross between the Nonpareil and the Texas.

Subsequent to its origination the present variety was topworked on older trees in the aforesaid experimental orchard, and such asexual reproductions—when they came into bearing—were found, by careful comparison, to carry forward all of the characteristics of the parent tree of the variety.

Figures 1, 2, 3:
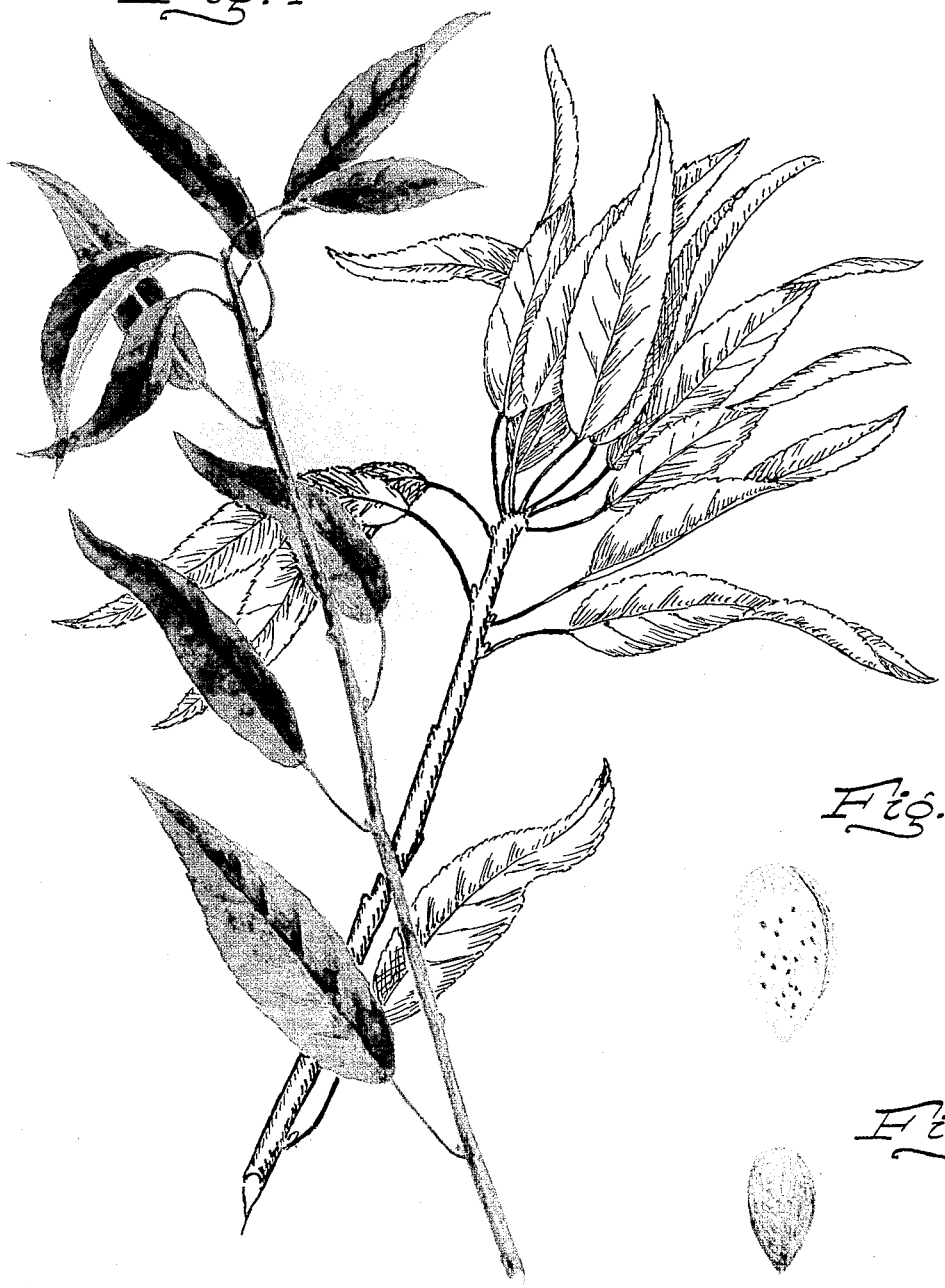
FIG. 1 is an elevation showing two shoots with leaves; one being represented in color. The view illustrates shoots cut in the autumn and after some of the leaves had fallen.
FIG. 2 is a view of one of the nuts after removal from the hull.
FIG. 3 is a view of one of the kernels.

Referring now more specifically to the botanical details of this new and distinct variety of almond tree, the following is an outline description thereof; all major color plate identifications being by reference to Maerz and Paul Dictionary of Color, except where common terms of color definition are employed:

*Tree*

Density: Open.
Size: Large to medium.
Vigor: Vigorous.
Branching habit: Medium to upright.
Foliage: Abundant.
- *Leaves.*—Size—Average. Margin—irregularly crenate, occasionally tends to be somewhat serrate toward apex, crenations average rather short and shallow. Color: Top side—medium green (22–L–7); under side—lighter green (20–J–5).
- *Bloom.*—Amount of bloom—heavy. Color—white. Blooming period—five or six days after the Texas and about ten days after the Nonpareil, in an average year.
- *Susceptibility or resistance to insects and diseases.*—No unusual susceptibility noted.

Crop:
- *Productivity.*—Very heavy.
- *Distribution of nuts on tree.*—Well distributed.
- *Ripening (harvest) period.*—Slightly later than the Texas.
- *Tenacity.*—Hangs on tree well.

Hull: Smooth; regular; thin.
- *Suture.*—Flat.
- *Color.*—Light green.
- *Dehiscence.*—Opening partially.
- *Splitting.*—Along suture.

Nut:
- *Size.*—Average length—1 3/16". Average width—13/16". Average thickness—5/8". Count by weight—about 200 to a pound.
- *Form.* — Length/width—1.6:1. Width/thickness—1.3:1.
- *Shell.*—Smooth. Outer shell—fairly hard. Inner shell—hard; well sealed.
- *Color.*—Medium light (9–B–3).
- *Pits.*—small; shallow; irregular.
- *Base.*—Square. Stem scar—small.
- *Apex.*—Acute; sharp; tip slightly recurved.
- *Wing.*—Narrow; thin; tapered toward apex.
- *Inner surface.*—Medium.
- *Ventral streak.*—Long.
- *Percentage of kernel to nut.*—52% to 58%—averaging 55%.

Kernel:
- *Size.*—Average length—7/8". Average width—1/2". Average thickness—9/32". Count by weight—about 28 to the ounce.
- *Form.* — Length/width—1.7:1. Width/thickness—1.7:1.
- *Base.*—Square. Stem scar—small.
- *Apex.*—Obtuse.
- *Plumpness.*—Smooth, with some striations.

*Pellicle.*—Thin.
*Pubescence.*—Smooth.
*Color.*—Light brown (13–L–10).
*Number of doubles.*—Few.
*Defective kernels.*—Practically none.
*Flavor.*—Normal.
*Quality.*—Good.

The tree and its nuts herein described may vary in slight detail due to climatic and soil conditions under which the variety may be grown.

The following is claimed:

A new and distinct variety of almond tree, as illustrated and described, characterized by a blooming period approximately five days later than the Texas and ten days later than the Nonpareil; by the heavy production of well sealed nuts comparable in size and quality to the Nonpareil; by a kernel shell-out percentage of approximately 55% as compared to 65% for the Nonpareil and 45% for the Texas; and by being interfertile with both the Texas and Ruby varieties.

No references cited.